(12) United States Patent
Halaka

(10) Patent No.: US 11,680,080 B2
(45) Date of Patent: Jun. 20, 2023

(54) PURIFICATION COLUMNS AND METHODS

(71) Applicant: Folim G. Halaka, Burr Ridge, IL (US)

(72) Inventor: Folim G. Halaka, Burr Ridge, IL (US)

( * ) Notice: Subject to any disclaimer, the term of this patent is extended or adjusted under 35 U.S.C. 154(b) by 450 days.

(21) Appl. No.: 14/208,758

(22) Filed: Mar. 13, 2014

(65) Prior Publication Data

US 2015/0259379 A1  Sep. 17, 2015

(51) Int. Cl.
  *C07K 1/18* (2006.01)
  *C07K 1/34* (2006.01)
  *C07K 14/765* (2006.01)

(52) U.S. Cl.
  CPC .......... *C07K 1/18* (2013.01); *C07K 1/34* (2013.01); *C07K 14/765* (2013.01)

(58) Field of Classification Search
  None
  See application file for complete search history.

(56) References Cited

U.S. PATENT DOCUMENTS

| | | |
|---|---|---|
| 3,948,775 A | 4/1976 | Otani et al. |
| 4,496,461 A | 1/1985 | Leeke et al. |
| 4,512,897 A | 4/1985 | Crowder, III et al. |
| 4,604,198 A | 8/1986 | Dailey et al. |
| 4,675,104 A | 6/1987 | Rai et al. |
| 4,676,898 A | 6/1987 | Saxena et al. |
| 4,743,373 A | 5/1988 | Rai et al. |
| 4,865,729 A | 9/1989 | Saxena et al. |
| 4,986,909 A | 1/1991 | Rai et al. |
| 5,200,150 A | 4/1993 | Rose, Jr. |
| 5,453,185 A | 9/1995 | Frechet et al. |
| 5,714,074 A | 2/1998 | Karlsson et al. |
| 5,935,429 A | 8/1999 | Liao et al. |
| 6,562,573 B2 | 5/2003 | Halaka |
| 6,652,745 B2 | 11/2003 | Gjerde et al. |
| 6,749,749 B2 | 6/2004 | Xie et al. |
| 7,074,331 B2 | 7/2006 | Allington et al. |
| 7,211,189 B2 | 5/2007 | Jinno et al. |
| 7,217,359 B2 | 5/2007 | Nakanishi et al. |
| 7,261,812 B1 | 8/2007 | Karp et al. |
| 7,479,223 B2 | 1/2009 | Dileo et al. |
| 8,158,002 B1 | 4/2012 | Lupton et al. |
| 8,496,819 B2 | 7/2013 | Shimizu et al. |
| 2002/0166769 A1 | 11/2002 | Serikov |
| 2003/0231981 A1 | 12/2003 | Johnson et al. |
| 2010/0276359 A1 | 11/2010 | Ippommatso et al. |

OTHER PUBLICATIONS

PCT Search Report and Written Opinion PCT/US15/20365 dated Jul. 1, 2015.
International preliminary report on patentability PCT/US15/20365 dated Sep. 13, 2016.
Raja Ghosh. Principles of Bioseparations Engineering. 2006 World Scientific Publishing Co. Pte. Ltd.
Noubar B. Afeyan et al. Perfusion Chromatography. 1990 Nature Publishing Group.

*Primary Examiner* — Kara M Peo
(74) *Attorney, Agent, or Firm* — Clifford H. Kraft

(57) ABSTRACT

Devices and associated processes suitable for small and large scale purification of molecules in a fluid, and provides embodiments that overcome the difficulties of transitioning purification from research stages to production scale-up. The invention relates to the formation and characteristics of substantially uniform, continuous, and homogeneous porous separation matrices. The matrices are in the form of a polymeric layer with substantially uniform thickness and porosity. The polymeric layer is formed for the purpose of providing convective flow through the separation matrix.

21 Claims, 9 Drawing Sheets

Detail A

*Prior Art*

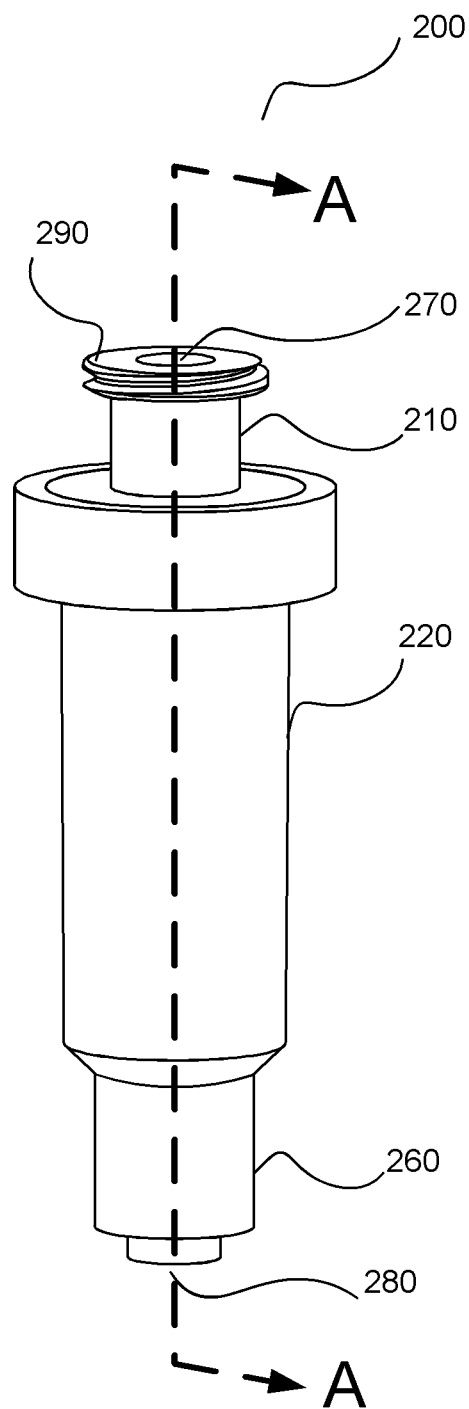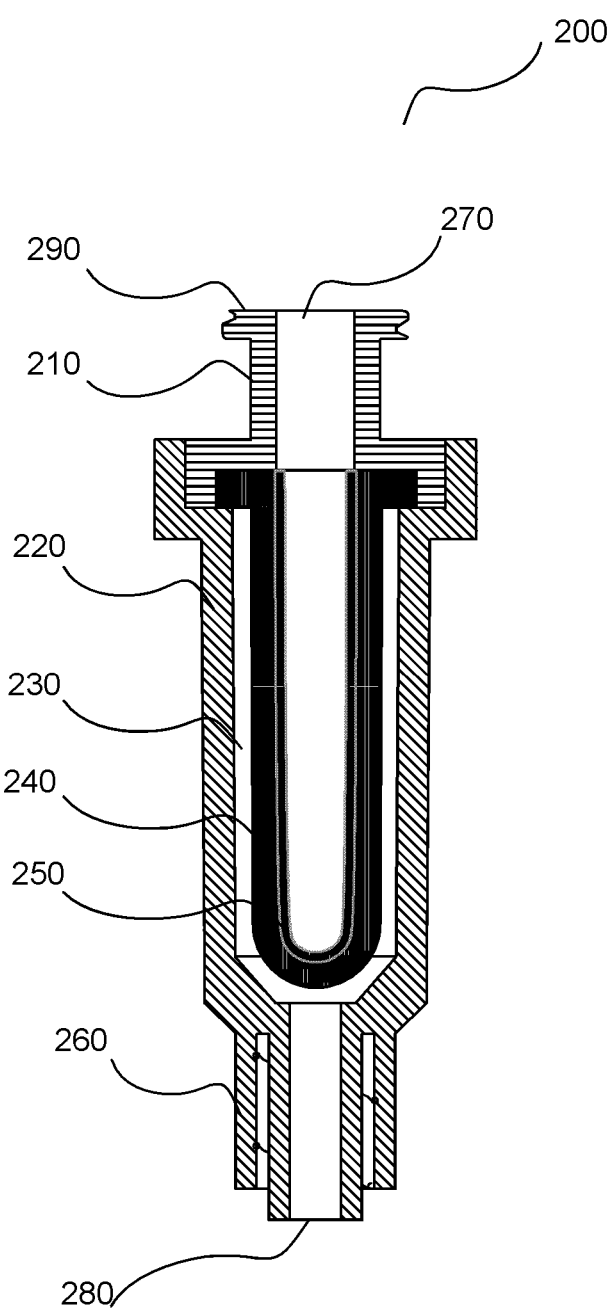
Figure 7
Figure 8

PURIFICATION COLUMNS AND METHODS

FIELD OF THE INVENTION

This invention relates to devices and methods for separation of solute(s) from mixtures thereof in solution. The present invention describes such devices, methods of their construction, and their application particularly for large scale purification of biomolecules, such as proteins.

BACKGROUND AND PRIOR ART

Chromatography and chromatographic columns are utilized in the vast majority of analytical and biological laboratories. The literature is therefore replete with scientific articles, text books, and patents on chromatography techniques. These techniques are sometimes referred to by the functionality of the chromatographic media, for example, ion-exchange, affinity, hydrophobic interaction, etc. Other references are sometimes inferred from the process or the physical characteristics of the process used, e.g., high performance liquid chromatography (HPLC), thin layer chromatography, hollow fibers, etc.

Purification is crucial to a host of industries, including the pharmaceutical, biotechnical, chemical, and food processing. In all, the purity of the product affects it efficacy, safety, cost, and general utility. Purification media affect the overall performance of the products being purified. For organism-made (genetically-engineered) drugs, purification needs are more complex as the purification process of genetically engineered human drugs often constitutes the largest share of their manufacturing cost. Additionally, sources of raw materials vary widely, and, in general, the component to be isolated represents a very small portion of the total quantity of the raw material.

In the present invention, by separation it is meant a process where all or a large number of components are separated, e.g., in chromatographic applications. By purification, it is meant the purification of a single, or a few compounds of interest, as in pharmaceuticals applications. The present invention's main purposes are toward application as purification tools. As such, the invention is distinguished with the advantage of not addressing the numerous aliquots characteristic of chromatography. Although the present invention is particularly directed toward purification, in some cases, the terms separation and purification are used interchangeably, and distinctions will be noted where warranted. Also, particles, particulates, and beads are used interchangeably.

Generally, purification media are present in two broad classes: polymeric particles, for example gel particulates (beads); and membrane-based products such as hollow fibers and flat sheets.

Gel beads are widely used as purification media. As the beads are not self-supporting, they are commonly packed in 'columns' e.g., chromatography columns. High capacity gel beads are porous throughout the inside of the beads. Packed beads columns possess unfavorable flow characteristics as will be detailed below. Some chromatographic particles were suggested to address flow shortcomings, e.g., Perfusive particles which possess larger through pores (U.S. Pat. No. 5,019,270).

Commercial-scale packed columns are of considerable size, particularly height, and thus require high pressure to achieve meaningful fluid flow. This imposes significant problems for large scale preparations where the columns are required to process hundreds of gallons, as in some fermentation applications. The high pressure requirement, which can be thousands of pounds per square inch (PSI), adds technical and cost challenges, may cause loss of potency if the target molecule is delicate, as is the case with many protein drugs. The high pressure can also deform and ultimately collapse the gel beads.

Membrane-based products, e.g., hollow fibers can be fast but their lower capacity limits their purification scale.

Monolithic-type columns have gained more use in recent years to provide improvements on chromatographic columns performance e.g., less band broadening, which aid in better band separation. They are small, usually in capillary form, see for example U.S. Pat. No. 6,210,570, and commercially available columns, e.g., Chromolith® columns, obtainable from Merck Co. Monolithic columns, because of their small size and flow rates are not suitable for large scale purification. Additionally, monolithic columns contain no lumen and thus are distinguished from the embodiments in the present invention.

Because of the interest and important applications, there exist numerous patents and scientific publications concerning the various aspects of separation and purification, in fields such as chromatography, electrophoresis, filtration, etc. Numerous forms of columns, separation media beds, and membranes have been described.

U.S. Pat. No. 8,496,819 to Shimizu et al, describes modification to monolithic columns with a filler layer encircling a monolithic rod.

U.S. Pat. No. 7,261,812 to Karp, et al., describes chromatographic separation devices that include multiple batch-processed columns joined by a body structure and adapted to perform parallel analyses. The invention deals with particulate-packed columns, where liquid-permeable frits of various types may be used to retain stationary phase material within columns.

U.S. Pat. No. 7,217,359 to Nakanishi, et al. describes a column for a liquid chromatograph having a honeycomb substrate including holes through which a sample flows and a separation phase filled in the holes. The honeycomb structure apparently forms capillaries to improve separations. An example is given for the separation of nitrobenzene from toluene. No guidance was given such that the body described in the invention can be assembled to give the advantages of the parallel flow described in the present invention; as it does not contain a lumen.

U.S. Pat. No. 7,211,189, (also U.S. Pat. No. 6,780,314) to Jinno, et al. describes a separation chromatography column, which comprises a hollow capillary containing long fibers as a stationary phase, with the long fibers packed inside the hollow capillary, and act to improve the gas and liquid chromatographic separation.

U.S. Pat. No. 7,074,331 to Allington, et al. describes permeable polymeric monolithic materials prepared in a column casing. In one embodiment, the permeable polymeric monolithic materials are polymerized while pressure is applied through a piston having a smooth piston head in contact with the polymerization mixture. The pressure eliminates wall effect, shrinkage and swelling. However, the remarks regarding monolithic columns stated above are applicable.

U.S. Pat. No. 6,749,749 to Xie, et al. describes a permeable polymeric monolithic materials prepared in a column casing, with improvements on swelling and wall effects. Refer to the comments above regarding such monolithic columns.

U.S. Pat. No. 6,652,745 to Gjerde, et al., describes a separation column and method for separating a mixture of double stranded DNA fragments by Matched Ion Polynucleotide Chromatography. The method uses a cylindrical column with an ID greater than about 5 mm and contains polymer beads. This will suffer from the variable flow rates through and around the beads as described herein, which the present invention offers solutions to alleviate.

U.S. Pat. No. 5,935,429, to Liao, et al. describes chromatography columns containing a continuous solid bed spanning the cross section of the column, the bed containing flow channels. Radial flow characteristics of the present invention are absent due to lack of a lumen in U.S. Pat. No. 5,935,429.

U.S. Pat. No. 5,714,074 to Karlsson, et al. describes improvements on methods of filling a liquid chromatographic column with particulate separation medium. The remarks on the disadvantages of packed particulates columns are to be considered.

U.S. Pat. No. 5,453,185 (also U.S. Pat. No. 5,334,310) to Frechet, et al. describes a process similar to monolithic columns, where the column containing a separation medium in the form of a macro porous polymer plug is disclosed. The column contains at least one macro porous polymer plug, prepared using a polymerization process described therein.

U.S. Pat. No. 5,200,150 (also U.S. Pat. No. 5,061,355) to Rose, Jr. describe a method of preparing a microcapillary gel separation column for electrophoresis comprises using photo initiator and forming a polymer plug by illuminating an initiation section of the tube.

U.S. Pat. No. 4,986,909 (also U.S. Pat. Nos. 4,743,373 and 4,675,104) to Rai, et al. describes chromatography column with a stationary phase that comprises a plurality of layers of swellable fibrous matrix in sheet form and having a spacer means between each layer for permitting controlled swelling, with means for distributing the sample through the stationary phase chamber segments.

U.S. Pat. No. 4,865,729 (and to a similar configuration in U.S. Pat. No. 4,676,898) to Saxena, et al., describes improvement on thin layer chromatography, having a horizontal flow of the liquid through the separating medium utilizing a fluid distribution system, the latter including a screen or mesh arrangement, and where the separation medium constitutes a thin layer, plate or wafer-like separation medium. The sample components are adsorbed onto the separation medium through the capillary action.

U.S. Pat. No. 4,604,198 to Dailey et al., discloses a multi-cartridge chromatography housing and fluid distribution, with a plurality of cartridge holders and an inlet fluid manifold means for distributing the fluid.

U.S. Pat. No. 4,512,897 to Crowder, III, et al. describes a separation column with a porous matrix of fiber having particulate immobilized therein, wherein at least one of the fiber or particulate is effective for molecular separation.

U.S. Pat. No. 4,496,461 to Leeke, et al., describes a chromatography column that comprises a swellable fibrous matrix in sheet form. The sheet is spirally wound around the longitudinal axis to form a plurality of layers around the axis.

U.S. Pat. No. 3,948,775 to Otani, et al., describes a horizontal multiple-chamber, packed column structure for adsorptive separation process wherein loading and unloading of packing material is facilitated, the packing material is described as particulate.

My U.S. Pat. No. 6,562,573 describes materials and methods usable for the purification of polyelectrolytes, such as nucleic acids and proteins, with separation media that possess pH-dependent groups with pKa value in the range of about 5 to about 7. Separation of the nucleic acids or proteins from a separation medium is effected at a neutral or higher pH.

SUMMARY OF THE INVENTION

The present invention describes devices, and associated processes, suitable for small and large scale purification of molecules in a fluid, and provides embodiments that overcome the difficulties of transitioning purification from research stages to production scale-up. The invention describes the formation and characteristics of substantially uniform, continuous, and homogeneous porous separation matrices. The matrices are in the form of a polymeric layer with substantially uniform thickness and porosity. The polymeric layer is formed for the purpose of providing convective flow through the separation matrix.

In the context of this invention, by convective flow it is meant a method for forcing a fluid into the pores of a matrix through, for example, the application of directional force gradient, e.g., a pressure differential in the transverse direction to the main axis of the separation matrix's layer. Convective flow is generally considerably faster than passive diffusion, as described in FIG. 1 below.

It is an important aspect of the present invention that uniformity in thickness and porosity forms consistent passageways for fluids and for molecules present in the fluids to be separated through the interaction with the separation matrix. This presents an improvement in terms of performance consistency, which is critical when multiple columns are used for large scale applications.

Additionally, when the porous separation matrix is modified such that it can interact with specific molecules, the matrix exhibits favorable binding and release characteristics of the aforementioned molecules. Modification of the porous separation matrix can be tailored to binding and release of particular molecule or a class of molecules.

Also described are embodiments to facilitate large volume, high flow rates, and low pressure applications, particularly where large quantities of fluids containing biopharmaceuticals and protein are to be processed. Due to the small wall thicknesses of the separation matrix in the present invention, high flow rates are achieved with lower pressures. Similar embodiments are suited for the purpose of environmental cleanup, e.g., large volumes of heavy metal contamination.

BRIEF DESCRIPTION OF THE DRAWINGS

FIG. 7 describes an elevated view of an embodiment of the present invention in a ready-to-use cylindrical column;

FIG. 8 describes a cross section of the ready-to-use column of FIG. 7;

DETAILED DESCRIPTION OF THE INVENTION

Figure 1:
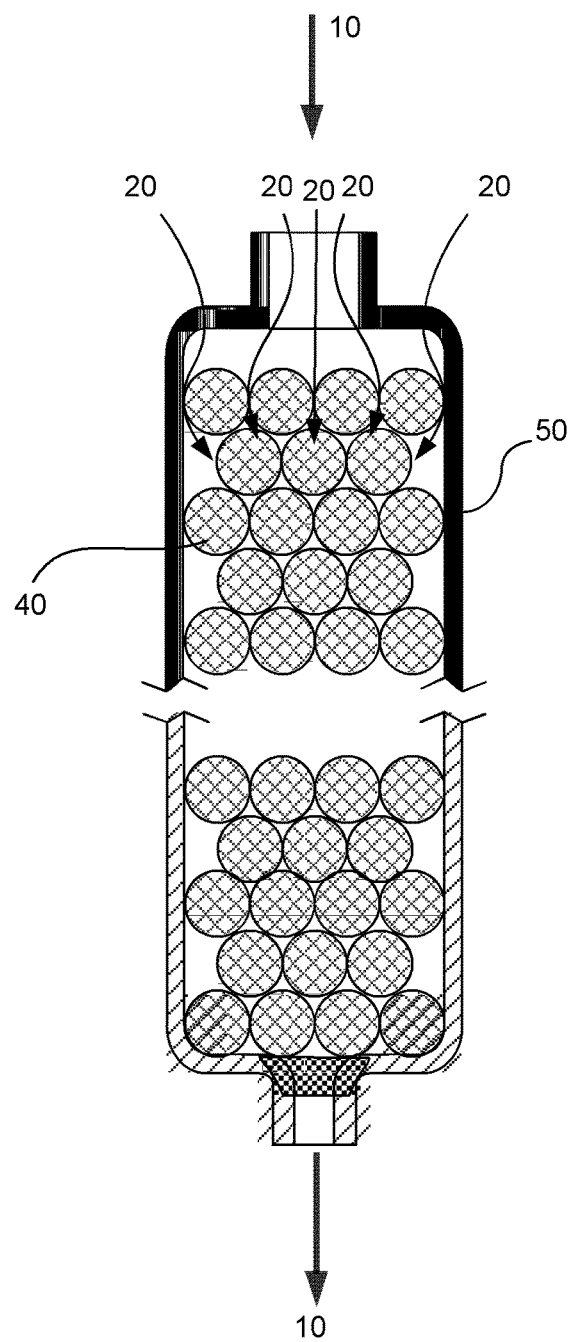
FIG. 1 describes fluid flow through a packed bead column in prior art and showing two distinct fluid flow patterns.

For clarity, unless otherwise stated: 'separation matrix' and 'polymeric separation matrix' are used interchangeably. By separation matrix it is meant a (thin) polymeric layer of continuous, homogeneous and of substantially uniform thickness and porosity; by uniform thickness it is meant that the thickness of the separation matrix's layer possesses variation less than 10% of nominal thickness, and preferably less than 5%. Similar uniformity characteristics is meant for separation matrix's layer porosity. Uniformity can be verified physically by direct measurement of thickness and pore diameter, using, e.g., high power microscopes and mercury porosimeters. However, uniformity is also indicated from performance of the binding and elution profiles. Efficient binding and concentrated elution in the first aliquots indicate uniform thickness and pore sizes.

By porous support it is meant an inert porous material of defined shape and porosity to serve as a support for the separation matrix. Porosity of the support is preferably equal to or larger than the porosity of the separation matrix. Porous support is preferably inert. By inert, it is meant that the support material is substantially passive, i.e., non-reactive either chemically (formation/breakage of chemical bonds) or physically (e.g., adhesion, hydrophobic interaction) with respect to components present in the fluid to be processed, particularly desired components therein. By separation element it is meant a basic element including a porous separation matrix and porous support. By separation device it is meant a physical device that can be used by an end user and including at least one separation element and means to receive and output fluid. By separation device assembly it is meant an assembly of separation devices, usually in the context of addressing larger fluid volumes.

The present invention describes novel formation of polymeric matrices for purification. The matrices possess substantially uniform porosity and bed depth (thickness) to render the matrices favorable to uniform flow, uniform binding and uniform release of (a) target component(s) in a fluid. The short bed depth (flow path) conditions allow for operating the columns under low pressures, an advantage when dealing with large volumes and delicate biomolecules. The matrices create efficient means to purify specific molecules in multi component fluids.

Control of matrix thickness uniformity ensures columns perform uniformly re: capture efficiency, and elution profile under the same environmental conditions, e.g., pressure, temperature, viscosity, etc. Columns prepared according to the present invention offer useful classes of purification devices, where parameters such as porosity, flux, functional group density, and spatial arrangements may be optimized to reproducibly address particular purification needs.

The matrices of this invention can be modified, e.g., by chemical reactions with specific functional groups, to specifically bind, or capture, specific molecules or a class of molecules with similar properties such as electric charge, size, shape, or hydrophobicity.

Figure 2:
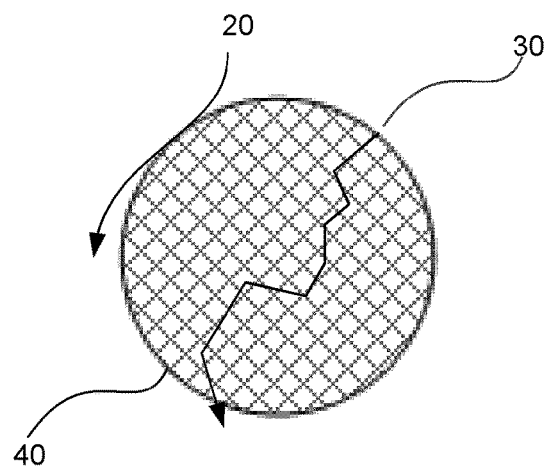
FIG. 2 is an exploded view of a single porous particle and describes fluid flow around and through the porous particle.

FIG. 1 presents an illustration of prior art using porous particulates 40 which are packed in chromatographic column casing 50. Fluid is fed to the column with total flow represented by arrow 10. The flow is then partitioned into separate flow components, e.g., through the voids between particulates 40 as presented by arrows 20, and through pores in the particulates. When particulates 40 are porous, some fluid flows into the inside of their pores, as illustrated in the magnified particulate in FIG. 2. The flow 20 through the voids between the particulate is primarily convective and can be enhanced by the application of higher pressure. The fluid flow through particulates' pores is mainly diffusive, as presented by rectilinear arrow 30 in FIG. 2. Note that increasing the pressure increases the velocity of the fluid passage around the particles, but does not significantly increase flow into the pores inside the beads. The two different flow rates lead to inhomogeneous binding and release characteristics as molecules in the fluid to be processed can readily interact with the surface of the particles, but to reach the inside of the particles, where most of the capacity for binding lies, the molecules must diffuse into the inside.

The pressure required to achieve practical flow rates through large particle packed columns thus described can be as high as thousands of pounds per square inch (PSI).

Figure 3:
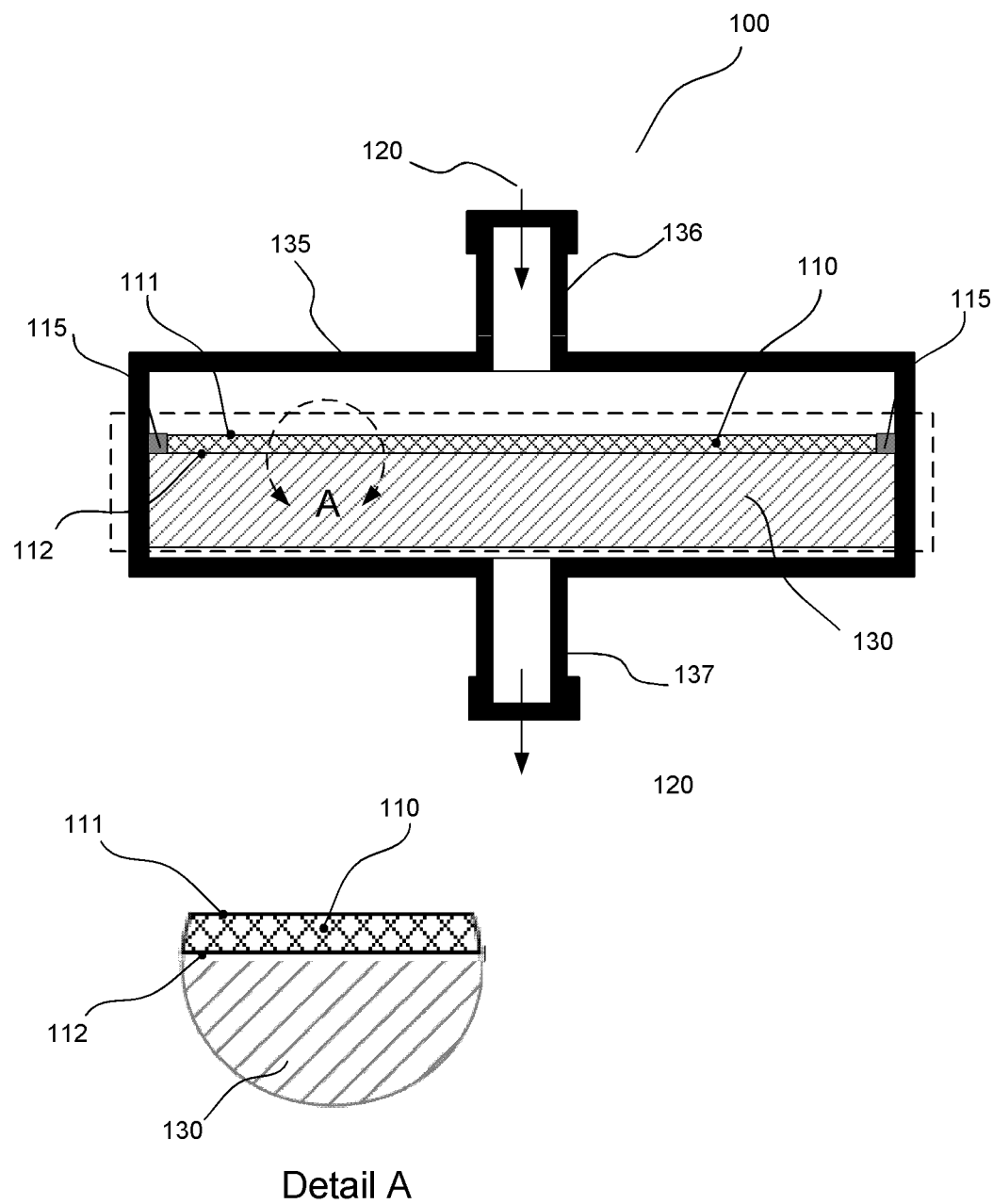
FIG. 3 describes a planar porous separation matrix element formation with substantial uniformity according to the present invention.

An important objective of the present invention is to present embodiments capable of processing fluids in substantially convective flow. FIG. 3 presents a cross section of such a separation device 100, including flat inert porous support 130 and porous separation matrix 110 and non-porous housing 135 with an inlet port 136 and an exit port 137 configured to define fluid flow directions. Non-porous gasket 115 is sealed to the top surface of flat inert porous support 130. Non-porous gasket 115 is preferably made of polyolefinic plastic or rubber. Non-porous gasket 115 aids in forming and shaping porous separation matrix 110 and in prevent fluid leakage around the circumferential edges of porous support matrix 130 and porous separation matrix 110. Porous separation matrix 110 is a homogeneous, continuous planar sheet and is supported by flat inert porous support 130. The bottom (or inner) surface 112 of porous separation matrix 110 is contiguous with the top surface of inert porous support 130 as shown in FIG. 3 (See Detail A). Fluid enters through inlet 136 and enters the pores of separation matrix 110, through the top (upper) surface 111. Note that the distance between top surface 111 and bottom surface 112 defines the thickness of the separation matrix 110. Fluid flow 120 increases and with applied pressure.

The outer circumferential sides of inert porous support 130 and gasket 115 form intimate contact with the inner wall of the non-porous housing 135. The intimate contact seals outer circumferential edges of inert porous support 130 and gasket 115 to non-porous housing 135, therefore preventing leakage and constrain the fluid to flow through the pores of the porous separation matrix 110. The intimate contact, or sealing, can be accomplished by a variety of methods, including but not limited to using adhesives, sonic welding, heat welding, spin welding, and heat welding.

The porous separation matrix can be formed from a variety of natural polymers, e.g., polysaccharides, or from chemically synthesized polymers. It is preferable that the matrix material possesses a phase transition, e.g., transition from liquid to gel (gellable polymer), which can be used to facilitate numerous embodiments in the present invention. For example, polysaccharides, e.g., agarose and dextran solutions are in a liquid state when heated and form solid, or semi-solid porous gels when cooled. In FIG. 3, the porous separation matrix is formed by casting, or pouring, onto flat porous support 130 a measured amount of solution of e.g., agarose while in liquid phase and allowing it to transition to gel phase by e.g., cooling the solution to form separation matrix 110. Transition to gel or semi-solid phase can also be achieved by cross linking of polymer solutions.

Depending on the polymer used, phase transitions can also be induced by change of ionic salt concentration, changes in the concentration of chelating agents, addition of metal ions, particularly polyvalent metal ions, such as calcium ions ($Ca^{+2}$), Copper ions ($Cu^{+2}$), Aluminum ions ($Al^{+3}$), etc. Positively charged metal ions would chelate with polymers containing electron-rich groups, such as amine and hydroxyl groups, to induce phase transition or gelling of liquid polymers. Polyvalent anions, such as phosphate ($PO_4^{-3}$), and carbonates ($CO_3^{-2}$), may also be utilized to induce phase transitions for polymeric materials containing positively charged or electron acceptor groups.

A similar effect can be achieved in the presence of chaotropic solutes e.g., urea or guanidinium salts, e.g., guanidinium hydrochloride or guanidinium thiocyanate, which are able to dissolve polysaccharides. Removal of the chaotropic solutes is observed to gel the polysaccharides.

Solutes in the fluid to be processed may interact with separation matrix 110, and after the fluid passes through pores of the inert porous support 130, the fluid exits through exit port 120.

Inert porous support 130 is preferably made from porous plastics such as polyolefin, ceramics, sintered glass or sintered metal. Inert porous support 130 provides a mechanical support towards preserving the mechanical structure and porous properties of porous separation matrix 110, particularly at high flow rates. For example, in FIG. 3, the flow in the direction of arrows 120 would under pressure tend to bend porous separation matrix 110 in the downward direction if inert porous support 130 is not incorporated. The resulting stress would alter the porous properties of the porous separation matrix and may lead to its rupture. The resulting stress would also be pressure-dependent, leading to variable distortion behavior. Additionally, the aforementioned stress limits the materials or polymers that may be used to form the porous separation matrix. An important aspect of the present invention is the presence of the inert porous support 130 to prevent such dimensional distortion and provide wider range of embodiments.

An additional inert porous support (not shown) may also be added to contact the outside (upper) surface 111 of porous separation matrix 110. In this embodiment, the additional inert porous support may be placed either before or after the formation of the separation matrix, in similar approach to those described herein. Although it might slightly complicate fabrication, the additional porous support provides additional mechanical protection to the porous separation matrix, the latter being now sandwiched between two inert porous supports, which would protect the separation matrix in cases where reversing the fluid flow direction is desirable for cleaning or regeneration of the separation device.

Figure 15:
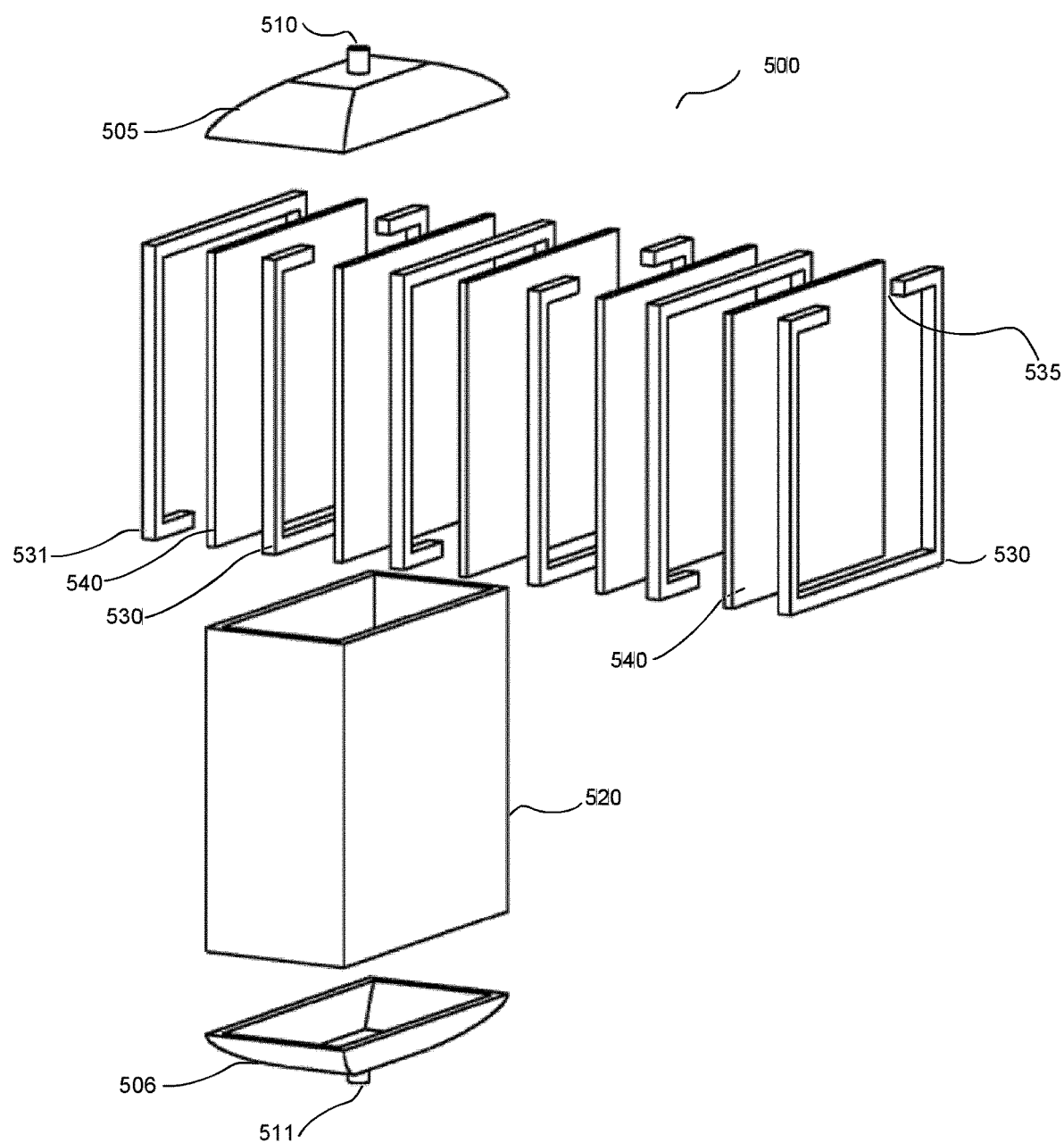

Inert porous support 130 with gasket 115 and separation matrix 110 are grouped (dashed line in FIG. 3) to form planar separation element 140, which will be useful when detailing embodiment where higher capacity devices use planar separation element 540 as repeating units, as shown in FIG. 15.

It is preferable that the separation matrix is contiguous with and bound to the inert porous support. In the present invention, since separation matrix formation starts with a fluid polymer solution, the polymer solution would occupy surface pores of the inert porous support, thus anchoring the porous matrix to the inert porous support. The polymer solution, due to its high viscosity, does not penetrate deep into the inert porous support without applying considerable pressure.

Furthermore, the porous separation matrix may be chemically cross-linked to the porous support matrix by the choice of the chemical composition of the inert porous support and the polymer forming the separation matrix. For example, if the porous support contains hydroxyl groups, e.g., cellulosic fibers, fiber glass, or silicates, the hydroxyl groups may be cross-linked to an appropriate group on the separation matrix.

Cross linking of the separation matrix to the porous support may be accomplished while the separation matrix is in liquid state or after it solidifies. Those with ordinary skill in the art would be able to effect cross linking with variety of cross linkers and procedures.

Porosity of the separation matrix can be controlled by the chemical composition and concentration of the polymer. Generally, more concentrated polymer solutions lead to smaller pores.

Figure 4:
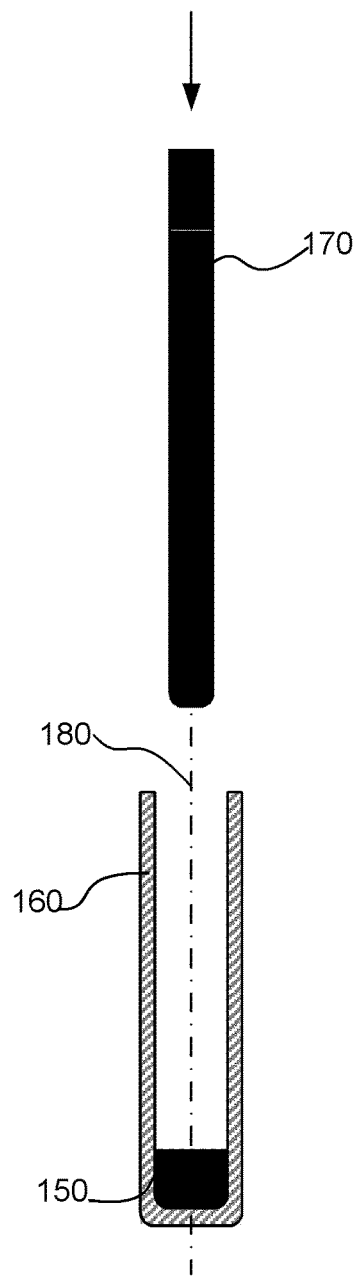
FIGS. 4, 5 and 6 describe the process of formation of a cylindrical uniform porous separation matrix.
Figure 5:
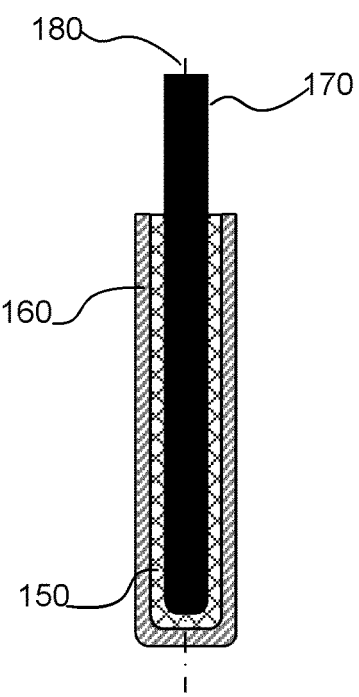
Figure 6:
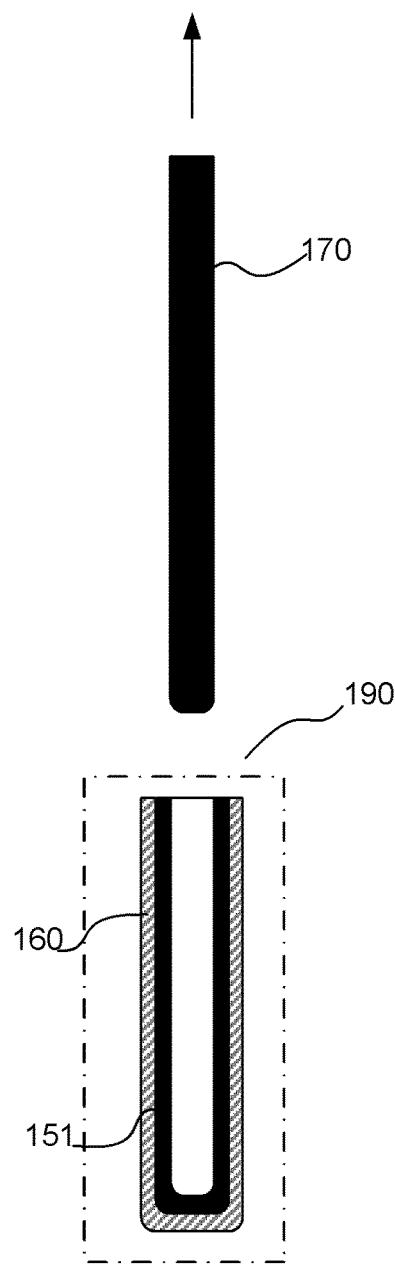

FIG. 4 through 6 present a process toward the formation of a cylindrical separation element 190:

In FIG. 4, polymer 150 is placed into the cavity (lumen) of inert porous hollow cylinder 160 while the polymer is in a fluid state. Plunger 170, a cylindrical rod, is aligned concentrically along the main axis 180 of inert porous cylinder 160. Plunger 170 has a diameter smaller than the inner diameter of inert porous cylinder 160. A substantially uniform gap is formed between plunger 170 and the inside walls of inert porous cylinder 160. The gap is equal to the difference between the inner radius of inert porous cylinder 160, and the radius of plunger 170. The gap controls the uniformity of the thickness of the porous matrix. Inert porous cylinder 160, similar to FIG. 3, acts to shape and supports the porous matrix. It is straightforward to calculate the volume of liquid polymer necessary to form the porous matrix from the geometry of the cylinders. A slightly larger volume may be used to ensure filling the gap between plunger 170 and the inner wall of inert porous support cylinder 160. A slightly larger volume may be used to also account for volume shrinkage due to phase changes from liquid to solid. Excess polymer is removed. Note that the uniformity of the gap just described depends on the dimensional precision of both the inner diameter of cylinder 160 and the diameter of plunger 170.

Note that different shapes, in addition to cylindrical, of porous support may be used, e.g., a conical shaped porous vessels. In this case, the plunger would be also of conical shape, with dimensions chosen to form a uniform gap between the inner wall of the porous support vessel and the outer walls of the plunger. Here, the conical porous support has inside base radius r1 and height h1, and plunger cone has a base radius r2 and height h2. The difference (h1–h2) is chosen to be equal to (r1–r2) and defines thickness of the porous separation matrix.

Referring to FIG. 5, while polymer 150 is in liquid form, plunger 170 is inserted into the cavity of the inert porous cylinder 160, and is stopped at a distance from the bottom of inert porous cylinder 160, the distance is equal to the thickness of the polymer layer formed in the gap between plunger 170 and the inner wall of inert porous cylinder 160. After the uniform porous separation matrix layer is formed, it is allowed to change phase or solidify. Solidification or gelling maybe accomplished by phase changing options described above, for example: lowering the temperature of the polymer solution; removal of a component from the polymer solution, e.g., salts or metal ions; addition of a component to the polymer solution, e.g., salts or metal ions; or, by cross linking of polymer 150 to form porous separation matrix 151.

Referring to FIG. 6, after uniform porous separation matrix 151 is formed and solidified, plunger 170 is withdrawn to form cylindrical (columnar) separation element 190, by carefully lifting upward. Cylindrical separation element 190 may be utilized for embodiment for higher capacity devices that use cylindrical separation element 190 as repeating units.

The inner diameter of the inert porous support in hollow cylindrical form is preferred to be precisely controlled, which can be accomplished by the use of available molded and machined hollow cylinders.

Plunger 170 is preferably made of inert material that does not stick, or bind, to the separation matrix, for example, polished steel and Teflon-coated steel. Plunger 170 may be coated with other coatings e.g., a hydrophobic coating, to prevent sticking of e.g., hydrophilic polymers to the plunger and facilitate withdrawal of plunger without distorting the uniform porous separation matrix.

The dimensions of the plunger, particularly the diameter, are chosen such that it precisely defines the thickness of the separation matrix. Also, the placement of the plunger is accurately controlled to achieve uniform thickness, the plunger is centered with the inert porous support so that its main (long) axis is precisely aligned with the main (long) axis of the porous support. This is preferably achieved by machined/molded fixtures and precise motion control mechanisms using, for example, stepper motors, computer-controlled movable stages and associated microprocessors.

The porous matrices just described possess several useful characteristics. One such useful characteristic is the presence of uniform passageways for fluid flow, which allow uniform flow throughout the whole separation matrix. Another favorable property is that low pressure would be sufficient to produce high fluid flow rates, due to the small thickness dimension of the formed porous separation matrix.

FIG. 7 shows an elevated view of a ready-to-use separation device 200 embodied according to the present invention. Separation device 200 is generally referred to as a column. FIG. 8 describes a cross section of the column in FIG. 7 along the A-A line. Separation device 200 includes a cylindrical separation element, similar to element 190 in FIG. 6, which includes porous separation matrix 250, which is formed inside an inert porous support cylinder 240. Inert porous support cylinder 240 is placed inside an inert, non-porous housing 220 and allowing gap 230 for fluid passage through the device. Inert porous cylinder 240 is bonded to top connector 210, which in turn is sealed to housing 220. The bonding may be accomplished by heat, sonication, or adhesive, and serves to force the fluid to flow through the lumen of the cylindrical separation and thus through the pores of porous separation matrix 250. Top connector 210 possesses an inlet port 270 to introduce fluid to be processed. Exit port 280 in housing 220 is used for fluid exit. Inlet port 270 and exit port 280 may possess luer fittings 290 or threaded connection 260 to facilitate connection to fluid delivery components.

The above embodiments facilitate the fabrication and use of the resulting device as a ready-to-used or disposable purification devices.

A major objective of the present invention is application to large scale purification. Purification devices similar to those described in FIG. 3 and FIG. 7 can be scaled up in variety of embodiments. For example, the dimensions of the separation element (planar separation element 140 or cylindrical separation element 190) can increase and thus afford more capacity. Although seems straightforward, this approach would eventually approach a limit of practical manufacturability and operating conditions.

A preferred approach is to connect multiple separation elements in parallel. Analogous to electrical resistor networks, connecting multiple resistors in parallel decreases resistance to electric current flow. Similarly, connecting separation elements in parallel decreases fluid flow resistance for the same flow rate.

Figure 11:
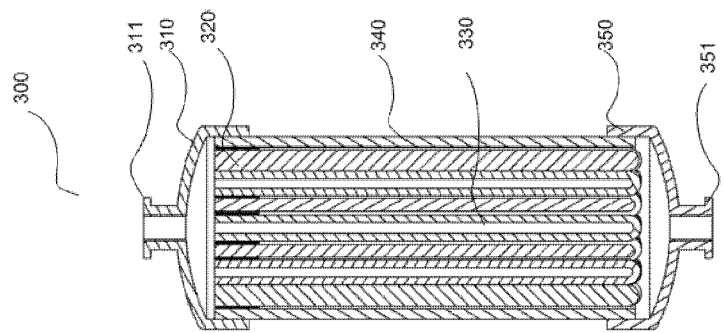
FIGS. 9, 10 and 11 describe a separation device including multiple cylindrical porous separation matrix elements.
Figure 10:
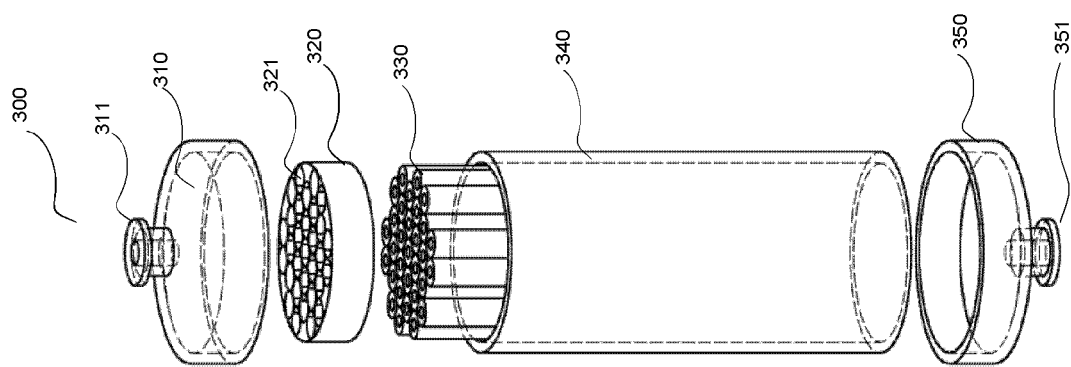
Figure 9:
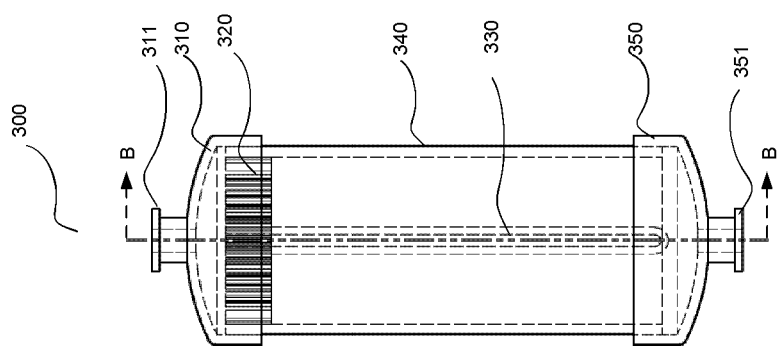

An embodiment representing a larger capacity separation device 300 is presented by applying parallel assembly of multiple cylindrical separation elements is presented in FIGS. 9 through 11. FIG. 9 shows a front view of a separation device (column) 300 including thirty one cylindrical separation elements 330. Cylindrical separation elements 330 are prepared in a similar method to that described in FIG. 4-7. Only a single cylindrical separation element is shown in FIG. 9 for clarity; refer to FIG. 10 which displays all separation elements. FIG. 10 shows an exploded view of the major components of separation device 300 in FIG. 9, and showing cylindrical separation elements 330, arranged to fit in a cylindrical housing 340. A sealing disc 320 includes openings 321 matching the geometry of the multiple cylindrical separation elements assembly. Sealing disc 320 seals the upper outer portions of cylindrical separation elements 330 to the inner walls of openings 321 of sealing disc 320 such that fluids are forced to flow through the lumen of the cylindrical separation elements 330, and thus through the pores of the separation matrix in a manner similar to that discussed in FIG. 7-8.

Bonding of sealing disc 320 to separation elements 330 may be accomplished by heat, sonication, spin welding, or adhesives. Cap 310 includes fluid inlet port 311 and cap 350 includes fluid exit port 351. Caps 310 and 350 are sealed to housing 340 to complete the construction of the assembly of multiple cylindrical separation elements. Further illustration is shown in FIG. 11, which shows a cross section of FIG. 9 across the B-B line.

Figure 12:
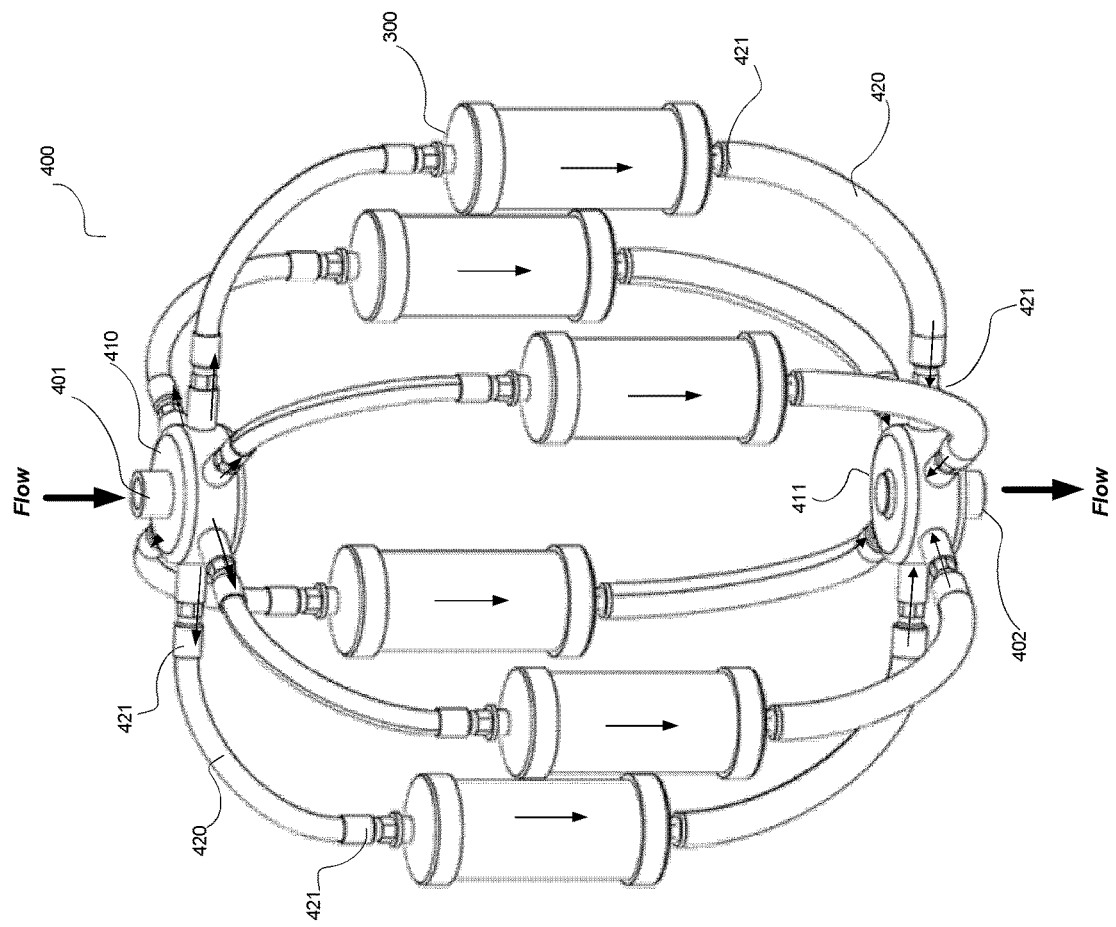
FIG. 12 describes a separation device including multiple separation cylindrical devices of FIG. 9.

Separation device assembly 300 can be further used to construct larger assemblies. For larger volume purification, e.g., in fermentation and biotechnology manufacturing applications, multiple separation devices 300 are assembled in parallel. FIG. 12 shows a separation device assembly 400 including six separation device assemblies 300. Referring to FIG. 12, separation device assembly 400 includes fluid distribution cap 410 which includes fluid entry port 401 and six outlet ports with fluid connectors 421, which connect tubing 420 to separation device assembly 300. Fluid distribution cap 411, for fluid exit, includes fluid exit port 402 and six outlet ports with fluid connectors 421. The arrows in FIG. 12 indicate fluid flow direction.

The separation device assembly described in FIG. 12 presents an innovative embodiment for large fluid volume processing. The reduction in pressure required for fast fluid processing offers major practical advantages: The larger the number of parallel units 300 the larger the drop of required pressure to process fluids at the same flow rate. Those with ordinary skill in the art will be able to configure additional separation units 300 by modification of fluid distribution caps 401 and 402, and associated tubing, connectors, etc.

Figure 14:
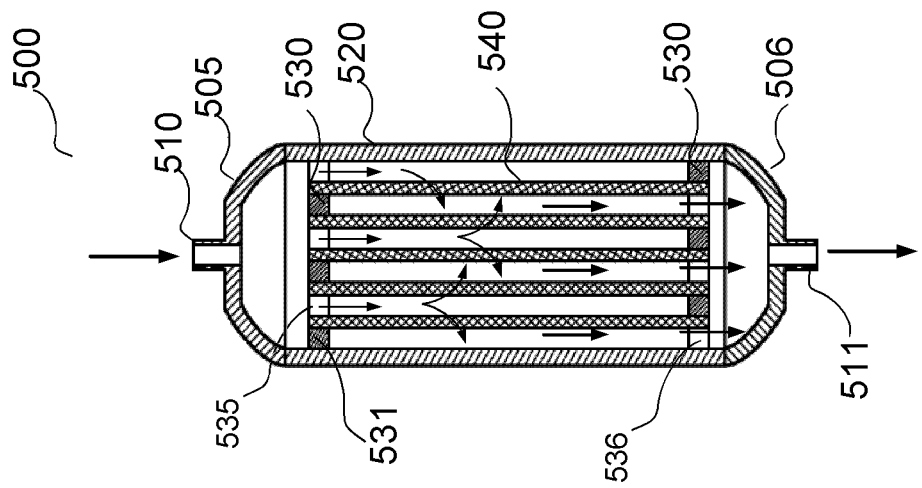
FIGS. 13, 14 and 15 describe a separation device including multi planar porous separation matrix elements; and, FIG. 16 describes the binding and release characteristics of a separation device modified to bind and elute anionic molecules in accordance with the present invention.
Figure 13:
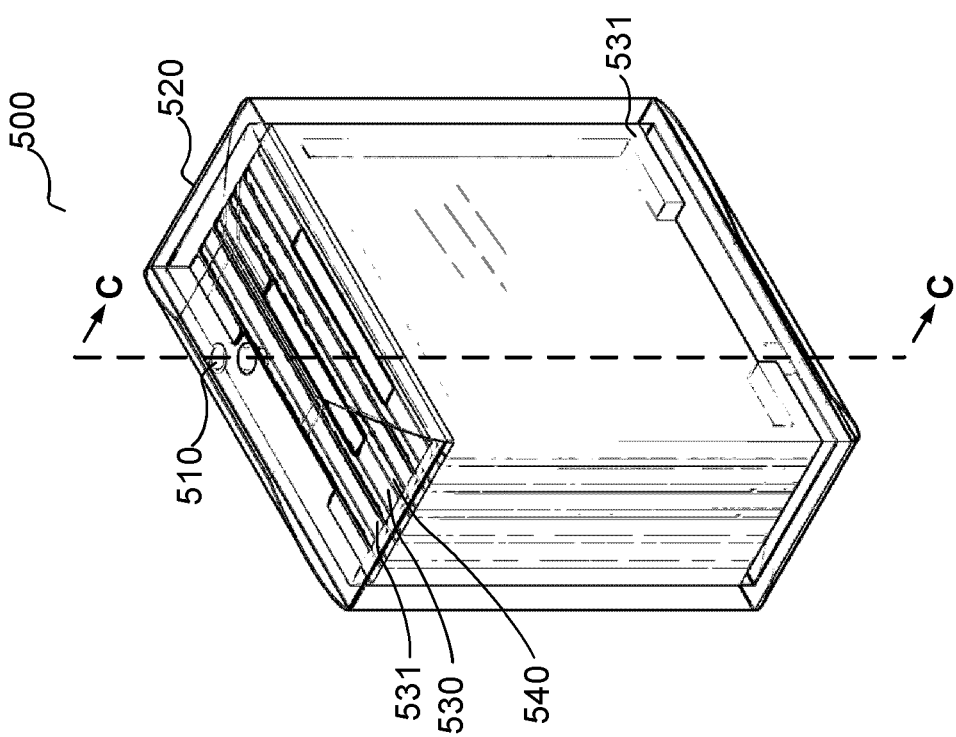

Further embodiments are illustrated using multiple planar separation elements 140 described in FIG. 3 above, in a similar fashion to the columnar device described in FIGS. 9-11. The embodiments are presented in FIG. 13 through FIG. 15. Referring to FIG. 13, separation device 500 includes parallel assembly of multiple flat sheet separation elements 540. FIG. 14 is a cross section of FIG. 13 along the C-C line. For clarification, FIG. 15 is an explosion of the components utilized in the embodiment. FIGS. 13-15 show an innovative embodiment to utilize the parallel arrangement of the planar separation elements 540, achieved by confining flow through equally spaced planar separation elements 540 by the use of non-porous gaskets 530 and 531. Referring to FIG. 15, fluid opening 535 is placed on top gaskets 530. Alternately, gasket 531 includes fluid opening 536 placed on the bottom. Fluid flow pathways are illustrated by the arrows in FIG. 15. Cap 505, including fluid inlet port 510, and cap 506, including fluid exit port 511 are sealed to enclosures 520. This arrangement allows fluid into the device and forces the fluid through the pores of planar separation matrices 540. An advantage of this embodiment is to allow parallel flow pathways to increase flow rates without increasing the applied pressure, as discussed above.

The above details of large scale applications illustrate the importance of uniformity of the separation matrix. In the absence of the control of the uniformity and the thickness and homogeneity of the porous separation matrix, efficient scale-up by using multiple separation elements would be difficult to achieve. This is an important aspect in the present invention, because if the thickness is non-uniform, the regions in the matrix with the smallest thickness will saturate its binding sites first. Afterwards, these regions are saturated early and become 'leaky' in that they permit target molecules to escape without capture while other regions can still capture such molecules. The controls thus described aid in achieving uniform and homogeneous porous separation matrices and allow efficient capture of target molecules, even at high flow rates. Also, a similar problem occurs when the bound molecules are to be released: molecules bound to the thinner regions in the capturing matrix will become "leaky" toward elution reagent leading to broad elution profiles, i.e., dilution of the purified compounds. Such characteristics are undesirable in separation devices.

PREFERRED EMBODIMENTS

In referring to the above discussion and illustrations, FIG. 3 presents a preferred embodiment of a planar porous separation matrix 150 possessing homogeneous physical properties when in liquid form and homogeneous thickness and porosity when in gel, semi-solid, or solid form.

In a particularly preferred embodiment, the porous separation matrix is derived from a polymer with the property of being in liquid form under certain conditions while becoming a gel under certain other conditions (gellable polymer).

Another preferred embodiment uses chaotropic solutes e.g., urea or guanidinium salts, e.g., guanidinium hydrochloride or guanidinium thiocyanate, to dissolve polysaccharides. Removal of the chaotropic solutes is observed to gel the polysaccharide.

In a preferred embodiment, the porous separation matrix is composed of complex polysaccharides, silicates, polyacrylates, polyimides, polyamides, and other polymers known to form porous matrices, and is preferably formed of agarose, cellulose, dextran and silica gels and hydrogels.

In another preferred embodiment, the porous separation matrix possesses homogeneous physical properties when in liquid form and homogeneous porosity when in gel, semi-solid, or solid form.

In a preferred embodiment, the porous separation matrix possesses uniform thickness, including the matrix's bottom when in cylindrical column format.

Thickness of the porous separation matrix depends on polymer material, height of the column, and pressure operational requirements. Thickness of the porous separation matrix may be between approximately 0.01 millimeter (mm) and 10 mm, and preferably between approximately 0.1 and 5 mm.

Porosity of the porous separation matrix is preferably between approximately 0.001 micrometers and 100 micrometers and preferably in the range of approximately 0.01 micrometers to 50 micrometers. Porosity for non-biological applications, e.g., metal ion binding is preferred to be on the low end of the above range.

Porosity of the porous support is preferably between approximately 0.01 micrometers and 500 micrometers and more preferably in the range of approximately 0.1 micrometers to 100 micrometers.

Thickness of the porous support is preferred to be between 0.1 mm and 50 mm, and more preferably between 1 mm and 10 mm.

In another preferred embodiment, the porous separation matrix is further cross-linked after its formation to further stabilize the porous separation matrix under flow conditions.

In another preferred embodiment, the inert porous support is chosen from a material capable of, or is chemically modified to enable its cross-linking to the porous separation matrix to further stabilize the porous separation matrix under flow conditions.

In a preferred embodiment, the porous separation matrix is chemically cross-linked to the surface of the porous support in order to further stabilize the porous separation matrix under flow conditions. Example 2 illustrates modification of the porous separation matrix by cross linking hydroxyl groups of the polysaccharide using epichlorohydrin.

In a preferred embodiment, the porous separation matrix is chosen to be capable of being modified to carry desirable functionalities of, for example, binding of proteins, nucleic acids, metal ions and other specific molecules. Example 3 illustrates modification of cross-linked porous separation matrix to carry a positive electric charge.

Those skilled in the art will be able to modify such a separation matrix with other functional groups familiar in the published art, for examples, weak and strong cation exchangers, weak and strong anion exchangers, filtration columns, hydrophobic, and affinity-based columns. Applications of such embodiments include purification of enzymes, oligomers, heavy metal ions, peptides, polysaccharides, carbohydrates, and sugars, e.g., fructose.

In a preferred embodiment, separation matrices functionalized to separate a class of proteins, or a well characterized individual protein by using an antigen-antibody (affinity) modification of the matrix. For example, the porous separations matrix can be modified to carry a first proteinaceous moiety that specifically binds a second proteinaceous moiety. Specifically, the first proteinaceous moiety can include antigens and the second proteinaceous moiety can include antibodies.

The porous separation matrix is preferred to be chemically modifiable to allow attachment of ligands, such as, but not limited to, cryptands and crown ethers, for the purpose of binding metals and other constituents.

In a preferred embodiment, and referring to FIG. 3, a method to construct a flat sheet separation device to separate solutes in a fluid sample mixture according to this invention, the separation device including:

Inducing a gellable polymer to be in a liquid state;

Casting a measured quantity of the liquid polymer onto the top surface of substantially flat horizontal inert porous support, whereby the gellable polymer forms a uniform thickness layer;

Inducing the polymer in the uniform thickness layer to gel; and,

Encasing the gelled polymer and the inert porous support in a non-porous housing, the non-porous housing includes fluid inlet and outlet fixtures configured to deliver and constrain sample mixtures to flow through pores in the porous separation matrix and collect purified solutes from the separation device.

Note that in the above embodiment a uniform porous gel sheet is formed by simply casting measured volume of a gellable fluid polymer onto a horizontal flat porous support, with the aid of gasket 115.

In a preferred embodiment, and referring to FIGS. 4-6 and to Examples 1-4, a method to construct a cylindrical separation device to separate solutes in a fluid sample mixture according to this invention, the method including:

Inducing a gellable polymer to be in a liquid state;

Adding a measured quantity of the liquid polymer into the lumen of a vertically oriented cylindrical inert porous support, the cylindrical inert porous support possesses an inside diameter (ID) and outside diameter (OD);

Placing a cylindrical rod concentrically with the major axis of the cylindrical inert porous support into the lumen of the cylindrical inert porous support, where the diameter of the cylindrical rod is less than that of the ID of the cylindrical inert porous support;

Inducing the gellable polymer to form a gel layer;

Upwardly lifting the cylindrical rod; and,

Encasing the gelled polymer and the inert cylindrical porous support in a non-porous housing, the non-porous housing includes fluid inlet and outlet fixtures configured to deliver and confine sample mixtures to flow through pores in the porous separation matrix and to collect purified solutes from the separation device.

The thickness of the porous separation matrix is equal to half the difference between the inner diameter of the cylindrical support and the diameter of the cylindrical rod. The thickness of the porous separation matrix therefore can be varied by changing the geometries of the cylindrical porous support and the cylindrical rod.

In a preferred embodiment, and referring to FIG. 3, a separation device for separation of a solute in a fluid sample using a planar separation element in a fluid and including:

a porous separation matrix with substantially uniform porosity and thickness. The thickness defines a distance between an inside surface and an outside surfaces of the porous separation matrix;

a substantially flat inert porous support contiguous with the outside surface of the porous separation matrix;

a non-porous housing encasing the flat inert porous support and the porous separation matrix, the non-porous housing includes fluid inlet and outlet fixtures configured to confine sample mixtures to flow through pores in the porous separation matrix and to collect purified solutes from the separation device, as illustrated in FIG. 7 through FIG. 11.

Note that the terms inside and outside are arbitrary, and are used only as means to label those surfaces.

In another preferred embodiment, and referring to FIGS. 4-7, a separation device for separation of a solute in a fluid sample, using a cylindrical separation element in a fluid and consists of:

a hollow inert cylindrical porous support;

a porous separation matrix with substantially uniform porosity and thickness, formed concentrically with the hollow cylindrical support, wherein the thickness defines a distance between an inside surface and an outside surface of the porous separation matrix;

a non-porous housing encasing the porous support and the porous separation matrix, the non-porous housing configured to define fluid flow of the fluid sample to pass through the pores of the porous separation matrix, the non-porous housing including an inlet port for fluid sample delivery and an outlet port for discarding undesired solutes and collection of desired solutes.

EXAMPLES

Example 1

2 grams of agarose, from Sigma Chemical Co, St. Louis, Mo., USA, were added to 100 milliliters (mL) of distilled water, and heated until completely dissolved. While still fluid, approximately 0.4 ml of the agarose solution was transferred to the lumen of porous high density polyethylene hollow cylinder similar to the cylinder in FIG. 4, obtained from Porex Crop. (Fairburn, Ga., USA). The hollow cylinder had dimensions measured at 35.4 mm high, 9.3 mm outside diameter (OD) and 4.5 mm inner diameter (ID). The volume of polymer solution needed can be calculated from the geometry of the column and plunger. The cylinder was positioned vertically, and immediately after the solution addition a 2.54 mm diameter Teflon-coated stainless steel rod (plunger), available from K-Mac plastics (Wyoming, Mich., USA), was placed in the center of cylinder (see FIGS. 4-6). The plunger was marked to indicate when its bottom location is at approximately 1 mm from the inside bottom of the porous support. The solution was allowed to cool to room temperature to gel/solidify for approximately two hours. Thereafter, the plunger was removed by carefully lifting vertically upward. The above process created a thin porous separation matrix (agarose) with substantially uniform thickness of approximately 1 mm inside the inert porous support cylinder. This example illustrates a process for a separation element that may be used as a filter separation element.

Example 2

The agarose in a separation element formed as in Example 1 was cross linked to increase stability of the polymeric separation matrix: The separation element was soaked in 100 milliliters (mL) of one molar sodium hydroxide (NaOH) for 150 minutes, followed by draining the NaOH solution. The cross linking was accomplished by soaking the cylinder in 95% ethanol/water mixture (volume/volume, V/V) containing 3% epichlorohydrin (V/V), with occasional stirring for about 14 hours, followed by draining the solution and washing four times by soaking in distilled water and draining. This example illustrates a separation element with cross-linked porous separation matrix that may be used as a filter separation element.

Example 3

A cross-linked separation element formed as in Example 2 was further modified to carry permanent positive electric charges by soaking in 1M NaOH followed by draining the NaOH solution. Thereafter, the separation element was soaked in 100 mL solution of 10% (weight/volume, W/N) of (2-☐Chloroethyl)☐trimethyl ammonium chloride (From Sigma Aldrich, Co., St. Louis, Mo., USA), prepared by dissolving 10 grams of (2-Chloroethyl) trimethyl ammonium chloride in 100 mL of 95% Ethanol/Water mixture (V/N). After soaking for 14 hours, the solution was drained out, followed by washing in distilled water and draining four times. This example illustrates a separation element with separation porous matrix that carries positive electric charges (quaternary ammonium ion) that may be used as an anion exchanger.

Example 4

Figure 16:
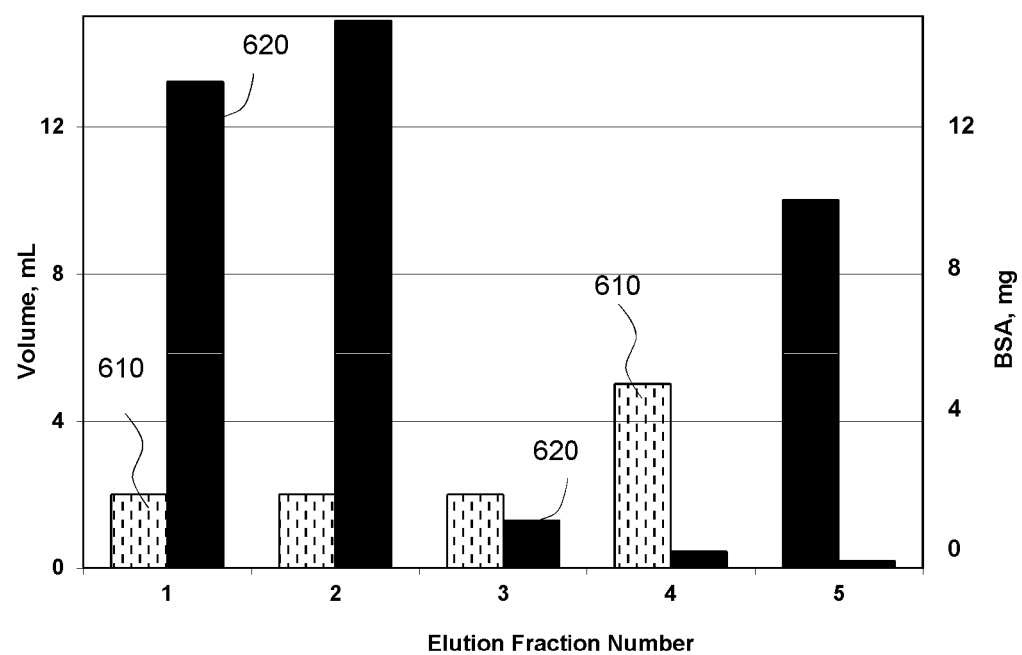

A luer fitting was attached to the open end of the quaternary ammonium ion separation element formed in Example 3. A plastic casing similar to the illustration in FIG. 7 was also attached and sealed to the luer fitting (see FIG. 7). The resulting separation device was used to bind and elute a negatively charged protein, bovine serum albumin (BSA). The separation device was washed with 15 millimolar (mM) Tris(hydroxymethyl)☐aminomethane buffer, pH=7 (Tris buffer). Five 10-mL aliquots of one milligram/mL (mg/mL) solution of bovine serum albumin (BSA) were passed through device by attaching the luer fitting to a syringe containing the BSA solution in the Tris buffer. Optical absorption at 280 nanometer (nm) wavelength was recorded for each aliquot after passage through the separation device, to calculate the amount of captured and escaped BSA. After loading of the protein, the device was washed with 10 mL of Tris buffer. Elution was effected by using 1000 mM sodium chloride (NaCl) solution in Tris buffer in three 1-mL aliquots, followed by one 5-ml aliquot and one 10-ml aliquot. Optical absorption at 280 nm was recorded for each elution aliquot. FIG. 16 shows the resulting elution profile of the separation device after passage of fifty mL buffer containing fifty mg of BSA in aliquots of ten ml as described above. The elution was accomplished by forcing the NaCl solution in aliquots (610) through the pores of the porous separation matrix. The amount of BSA in each aliquot (620) was calculated spectrophotometrically through absorption at 280 nm, with applicable dilution correction. The device shows concentrated elution of bound BSA, with over 90% percent of the bound BSA eluted in the first four mL of elution. This example illustrates the use of a separation device as an anion exchanger according to the present invention.

Several descriptions and illustrations have been presented to aid in understanding the present invention. One with skill in the art will realize that numerous changes and variations may be made without departing from the spirit of the invention. Each of these changes and variations is within the scope of the present invention.

I claim:

1. A separation device for separating a solute in a fluid sample, said device comprising:
    (a) a porous support forming a first layer defining a first surface and a plurality of first pores;
    (b) a porous separation matrix forming a continuous, homogeneous second layer, said second layer defining a second surface and a plurality of substantially uniform second pores and thickness, said second surface being placed on and contiguous with said first surface, wherein said second pores define through passageways configured to establish convective flow of the fluid sample through the through passageways;
    (c) a functional group that is attached to the porous separation matrix and captures the solute from the fluid sample convectively flowing into the through passageways of the second pores; and
    (d) a non-porous housing encasing said porous support and said porous separation matrix, the non-porous housing including an inlet port for entry of the fluid sample and an outlet port through which the fluid sample exits the non-porous housing, wherein, the non-porous support and the porous separation matrix are configured to force said fluid sample under pressure to flow convectively through the through passageways.

2. The separation device of claim 1 wherein said porous separation matrix is formed from a polymeric material.

3. The separation device of claim 2 wherein the polymeric material of said porous separation matrix comprises a member of the group consisting of a: polysaccharide, silicate, polyacrylate, polyimide, and polyamide.

4. The separation device of claim 1 wherein said porous separation matrix is cross linked.

5. The separation device of claim 1 wherein the functional group of said porous separation matrix comprises a negative electric charge or a positive electric charge that attracts an oppositely-charged portion of the solute.

6. The separation device of claim 1 wherein the functional group of said porous separation matrix comprises a first proteinaceous moiety that specifically binds a second proteinaceous moiety.

7. The separation device of claim 6 wherein said first proteinaceous moiety includes antigens and the second proteinaceous moiety includes antibodies.

8. The separation device of claim 1 wherein the functional group of said porous separation matrix is modified with a chemical group for binding heavy metal ions.

9. The separation device of claim 1 wherein said porous support is non-reactive towards solutes in said fluid sample.

10. The separation device of claim 9 wherein said porous support is one of the group consisting of polyolefin, ceramic, sintered metal and sintered glass.

11. The separation device of claim 1 wherein said porous support is cross linked to said porous separation matrix.

12. The separation device of claim 1 wherein the porous separation matrix has a thickness between approximately 0.01 mm to 10 mm.

13. The separation device of claim 1 wherein porosity of said porous separation matrix is approximately between 0.001 to 100 micrometers.

14. The separation device of claim 1 wherein thickness of said porous support is between approximately 0.1 mm to 50 mm.

15. The separation device of claim 1 wherein porosity of said porous support is approximately 0.01 to 500 micrometers.

16. A plurality of the separation devices of claim 1, wherein said plurality of separation devices are arranged in parallel, wherein the inlet port of each device shares a common connection and wherein the outlet port of each device also shares a common connection.

17. The separation device of claim 1, wherein the porous support and the porous separation matrix are arranged so the fluid sample sequentially encounters the porous support and the porous separation matrix.

18. The separation device of claim 1, wherein the porous support and the porous separation matrix are arranged so the fluid sample convectively flows through an interface between the porous support and the porous separation matrix.

19. The separation device of claim 1, wherein the second layer of the porous separation matrix is external of the first pores defined by the porous support.

20. The separation device of claim 1 further comprising a second porous support forming a third layer that is separated from the first layer by the second layer.

21. The separation device of claim 1, wherein the porous separation matrix comprises a main axis, and the porous separation matrix is arranged within the non-porous housing so the fluid sample convectively flows under an applied pressure differential in a transverse direction relative to the main axis of the porous separation matrix.

\* \* \* \* \*